United States Patent [19]

Tseng

[11] 4,411,690

[45] Oct. 25, 1983

[54] FUSED [1,2,4]OXADIAZOLYLIDENEBENZENESULFONAMIDES AND THEIR USE AS HERBICIDES AND PLANT GROWTH REGULANTS

[75] Inventor: Chi-Ping Tseng, Wilmington, Del.

[73] Assignee: E. I. Du Pont de Nemours & Co., Wilmington, Del.

[21] Appl. No.: 326,267

[22] Filed: Dec. 3, 1981

Related U.S. Application Data

[63] Continuation-in-part of Ser. No. 228,705, Jan. 26, 1981, abandoned.

[51] Int. Cl.³ .................... A01N 43/90; C07D 498/04
[52] U.S. Cl. .......................................... 71/92; 71/93; 544/215; 544/255
[58] Field of Search .................. 544/212, 255; 71/92, 71/93

[56] References Cited

U.S. PATENT DOCUMENTS

| 3,637,366 | 1/1972 | Wietelmann et al. | 71/103 |
| 4,150,131 | 4/1979 | Muller et al. | 544/255 |
| 4,225,537 | 9/1980 | Levitt | 71/92 |

Primary Examiner—Paul M. Coughlan, Jr.

[57] ABSTRACT

Fused [1,2,4]oxadiazolylidenebenzenesulfonamides such as 2-chloro-N-(5,7-dimethyl-2H-[1,2,4]oxadiazolo-[2,3-a]pyrimidin-2-ylidene)benzenesulfonamide and 2-chloro-N-(7-methoxy-5-methyl-2H-[1,2,4]oxadiazolo-[2,3-a][1,3,5]triazin-2-ylidene)benzenesulfonamide are general and selective pre- or post-emergence herbicides and can be useful in regulating plant growth.

33 Claims, No Drawings

FUSED [1,2,4]OXADIAZOLYLIDENEBENZENESULFONA-MIDES AND THEIR USE AS HERBICIDES AND PLANT GROWTH REGULATORS

RELATED APPLICATION

This application is a continuation-in-part of my copending application U.S. Ser. No. 228,705, filed Jan. 26, 1981, now abandoned.

BACKGROUND OF THE INVENTION

This invention relates to novel fused [1,2,4]oxadiazolylidenebenzenesulfonamides and to their use as general and selective pre- or post-emergence herbicides and as plant growth regulants.

U.S. Pat. No. 3,154,548 discloses compounds of the formula:

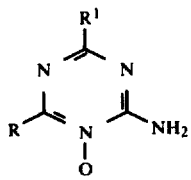

where

R is alkyl, halo- and aryl-substituted alkyl, aryl and halo-, nitro-, and alkyl-substituted aryl; and $R^1$ is alkyl, hydroxy- and arayl-substituted alkyl, aryl and halo-, nitro- and alkyl-substituted aryl. The compounds are described as chelating agents.

B. Bobranski et al., in *Arch. Immunol. Theor. Exp.*, 16 (5), 804 (1968) disclose the compound:

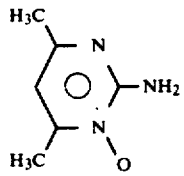

No utility was disclosed in the abstract.

R. Gompper et al. in *Chem. Ber.*, 99, 2900 (1966) discloses compounds of the formula:

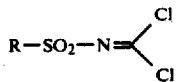

where

R is $CH_3$, $C_6H_5$, p—Cl—$C_6H_4$ and p—$CH_3$—$C_6H_4$. These compounds are taught to be intermediates.

M. Hamana et al. in *Chem. Pharm. Bull.*, 22 (7), 1506–1518 (1974) disclose the compound:

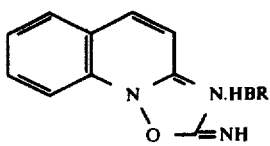

No utility is taught.

SUMMARY OF THE INVENTION

The present invention relates to novel compounds of Formula I, to compositions containing them and to their use as general and selective pre- or post-emergence herbicides and as plant growth regulants.

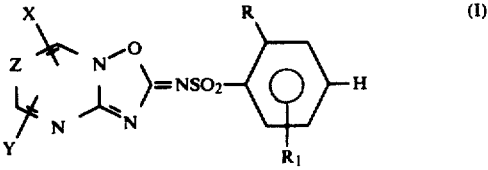

where

R is $C_1$-$C_4$ alkyl, $C_1$-$C_1$ alkoxy, F, Cl, Br, $NO_2$, $COR_4$, $SO_2R_5$, $SO_2NR_6R_7$, $SO_2OCH_2CF_3$, $SO_2OCH_2CCl_3$, $SO_2N(OCH_3)(CH_3)$, $BR_8$, $OSO_2R_9$ or $CH_2P$;

$R_1$ is H, F, Cl, Br, $CF_3$, $NO_2$, $C_1$-$C_4$ alkyl or $C_1$-$C_4$ alkoxy;

$R_4$ is $C_1$-$C_6$ alkoxy, $C_3$-$C_6$ alkenyloxy, $C_2$-$C_6$ haloalkoxy substituted with 1–3 atoms selected from F, Cl, or Br, $C_5$-$C_6$ cycloalkoxy, —$O(CH_2CH_2O)_nR_{10}$ or $OCH_2CH_2CH_2OR_{10}$;

n is 1 or 2;

$R_5$ is $C_1$-$C_4$ alkyl;

$R_6$ and $R_7$ are independently $C_1$-$C_4$ alkyl, provided the total number of carbon toms of $R_6$ and $R_7$ does not exceed 5;

B is O or $SO_2$;

$R_8$ is $CHF_2$, $CF_3$, $CH_2CF_3$, $CF_2CHFG$ where G is F, Cl, Br or $CF_3$;

$R_9$ is $C_1$-$C_4$ alkyl or $C_1$-$C_4$ alkyl substituted with 1–3 atoms selected from F, Cl or Br;

P is $C_1$-$C_4$ alkoxy, $C_3$-$C_4$ alkenyloxy or $SO_2R_5$;

$R_{10}$ is $CH_3$ or $CH_3CH_2$; X is $CH_3$, $CH_3CH_2$, $CH_3O$ or $CH_3CH_2O$;

Y is H, Cl, $CF_3$, $C_1$-$C_4$ alkyl, $C_1$-$C_4$ alkoxy, $CH_2OCH_3$, $CH_2OCH_2CH_3$, $CH_2CH_2OCH_3$ or $CH_2CH_2OCH_2CH_3$; and Z is CH or N.

Preferred in order of increasing activity and/or increasingly favorable ease of synthesis are those compounds of Formula I wherein:

(1)
R is $C_1$-$C_4$ alkyl, $C_1$-$C_4$ alkoxy, F, Cl, Br, $CF_3$, $SO_2R_5$, $BR_8$, $OSO_2R_9$ or $CH_2P$, where P is $C_1$-$C_4$ alkoxy; and
$R_1$ is H, F, Cl, Br, $CF_3$, $C_1$-$C_4$ alkyl or $C_1$-$C_4$ alkoxy.

(2) Compounds of preferred (1) wherein $R_1$ is H.

(3) Compounds of preferred (2) wherein
R is $C_1$-$C_3$ alkyl, $C_1$-$C_3$ alkoxy, F, Cl, Br, $CF_3$, $SO_2R_5$, $BR_8$, $OSO_2R_9$ or $CH_2P$;
provided that:
  (a) when R is $SO_2R_5$, then $R_5$ is $C_1$-$C_3$ alkyl;
  (b) when R is $BR_8$, then $BR_8$ is $SO_2CF_3$ or $OCF_2CF_2H$;
  (c) when R is $OSO_2R_9$, then $R_9$ is $C_1$-$C_3$ alkyl or $CF_3$; and
  (d) when R is $CH_2P$, then P is $CH_3O$.

(4) Compounds of preferred (3) wherein
Y is H, $CF_3$, $C_1$-$C_2$ alkyl, $C_1$-$C_2$ alkoxy or $CH_2OCH_3$.

(5) Compounds of preferred (4) wherein
X is $CH_3$ or $CH_3O$; and Y is $CH_3$ or $CH_3O$.

Specifically preferred for high activity and/or ease of synthesis are the following compounds of Formula I:

2-Chloro-N-(5,7-dimethyl-2H-[1,2,4]oxadiazolo[2,3-a]pyrimidin-2-ylidene)benzenesulfonamide;

2-Chloro-N-(5-methoxy-7-methyl-2H-[1,2,4]oxadiazolo[2,3-a]pyrimidin-2-ylidene)benzenesulfonamide;

2-Chloro-N-(7-methoxy-5-methyl-2H-[1,2,4]oxadiazolo[2,3-a][1,3,5]triazin-2-ylidene)benzenesulfonamide; and 2-Chloro-N-(7-methoxy-5-methyl-2H-[1,2,4]oxadiazolo[2,3-a][1,3,5]triazin-2-ylidene)benzenesulfonamide.

This invention also relates to novel compounds of Formula II which are valuable intermediates for the preparation of herbicides of this invention.

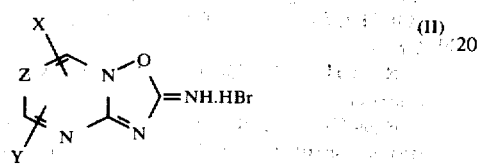

wherein

X, Y and Z are as previously defined.

Preferred Intermediates, in order of increasingly favorable ease of synthesis and/or high activity of the herbicides of Formula I, are compounds of Formula II wherein:

(1) Y is H, $CF_3$, $C_1$-$C_2$ alkyl, $C_1$-$C_2$ alkoxy or $CH_2OCH_3$.

(2) Compounds of preferred (1) wherein X is $CH_3$ or $CH_3O$, and Y is $CH_3$ or $CH_3O$.

DETAILED DESCRIPTION OF THE INVENTION

Synthesis

Many of the compounds of Formula I can be prepared by reacting an aminoheterocyclic-N-oxide of Formula III with an N-(substituted phenylsulfonyl)carbonimidic dichloride of Formula IV as shown in Equation 2. Compounds of Formula IV can be prepared from dimethyl-N-(substituted phenylsulfonyl)carbonimidodithioates of Formula V by treatment with a chlorinating agent such as sulfuryl chloride, as shown in Equation 1.

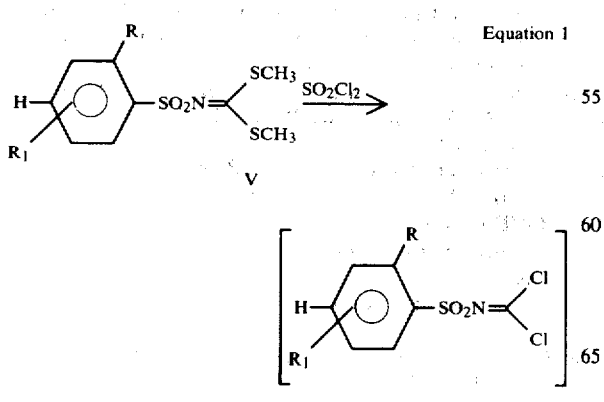

Equation 1

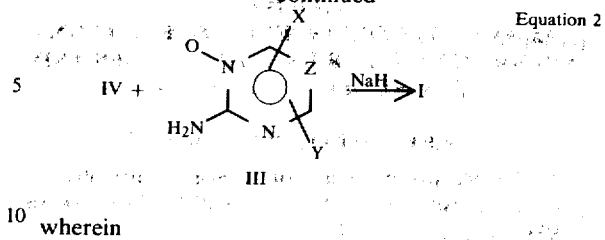

Equation 2 wherein

R, $R_1$, X, Y and Z are as previously defined.

The reaction of Equation 1 is best carried out in an inert aprotic organic solvent such as methylene chloride or chloroform at ambient pressure and temperature. The mode of addition is not critical; however, it is often convenient to add the sulfuryl chloride to a solution of the compound of Formula V. Since the sulfuryl chloride is a liquid, its addition can be easily controlled.

The product of Formula IV can be isolated by concentration of the reaction mixture under reduced pressure, and it may be used in the subsequent step without intermediate purification.

The reaction of Equation 2 is best carried out in an inert aprotic organic solvent such as tetrahydrofuran or ethylene glycol dimethyl ether, at ambient pressure and temperature. It is often convenient to first mix the reactants III and IV in an inert solvent and then add sodium hydride in portions to this mixture. The desired product is isolated by evaporation of solvents, addition of the concentrated reaction mixture to water and filtration. The product can be purified by washing with ether.

Alternatively, compounds of Formula I may also be prepared by reacting an appropriately substituted benzenesulfonyl chloride of Formula VI with an 1,2,4-oxadiazlo[2,3-a]heterocyclicimine hydrobromide of Formula II, as shown in Equation 3:

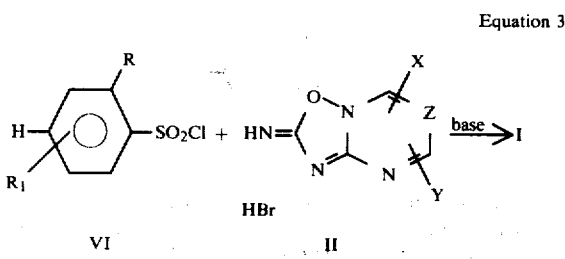

Equation 3 wherein

R, $R_1$, X, Y and Z are as previously defined.

The reaction of Equation 3 may best be carried out in inert aprotic organic solvents such as methylene chloride or tetrahydrofuran at a temperature in the range of about $-20°$ C. to $10°$ C. Two equivalents of a base such as trimethylamine, triethylamine, DABCO or sodium hydride may be used. It is often convenient to mix VI and II in an inert solvent first and then add base in portions to this mixture.

The desired product of Formula I may be isolated by filtration and concentration of the filtrate. The crude product may be further purified by column chromatography.

A. Carbonimidodithioate Intermediates

Many of the intermediate dimethyl N-(substituted phenylsulfonyl)carbonimidodithioates of Formula V can be prepared by treatment of corresponding arylsulfonamides with carbon disulfide and potassium hydroxide followed by reaction of the dipotassium salt with methyl iodide as shown in Equation 4.

Equation 4

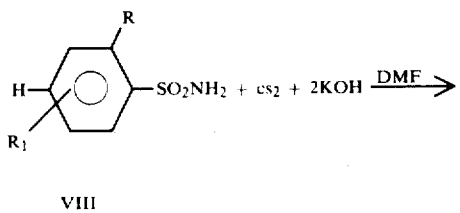

VIII

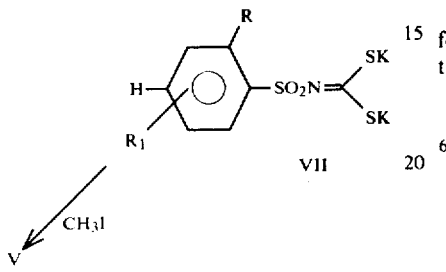

VII

V wherein
R and $R_1$ are as previously defined except in those instances where R is $COR_4$ or $NO_2$.

The arylsulfonamide is dissolved in dimethylformamide (DMF) with an equivalent amount of carbon disulfide and two equivalents of potassium hydroxide are added in portions at ambient pressure and temperature. The mixture is stirred for 1-8 hours and methyl iodide is then added to the stirred suspension at ambient pressure and temperature. The mixture is then stirred for another 2-6 hours. The dimethyl N-(substituted phenylsulfonyl)carbonimidodithioate which is formed can be isolated by addition of the reaction mixture to water and filtration. The product can be purified by washing with a solvent such as ether or hexane.

The preparation of sulfonamides from ammonium hydroxide and sulfonyl chloride is widely reported in the literature, e.g., Crossley et al., *J. Am. Chem. Soc.*, 60, 2223 (1938).

Certain sulfonyl chlorides are best prepared by chlorosulfonation of a substituted benzene in carbon tetrachloride according to the teaching of H. T. Clarke et al., *Org. Synth.* Coll. Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960).

Many of the intermediate dimethyl N-(substituted phenylsulfonyl)carbonimidodithioates of Formula V may also be prepared by reacting an appropriately substituted arylsulfonamide with tri(methylthio)methyl tetrafluoroborate as shown in Equation 5.

Equation 5

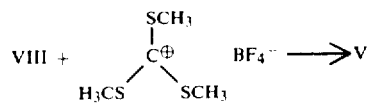

wherein
R and $R_1$ are as previously defined.

The reaction of Equation 5 may best be carried out in inert aprotic organic solvents such as methylene chloride or chloroform at 0° C. to 60° C.

The dimethyl N-(substituted phenylsulfonyl)carbonimiodoithioate of Formula V may be isolated by evaporation of the solvent, trituration of the residue with water and filtration. The product may be purified by washing with a solvent such as ether or hexane.

Tri(methylthio)methyl tetrafluoroborate can be prepared from dimethyl carbonotrithioate and trimethyloxonium fluoroborate according to the procedure taught by W. P. Tucker and G. L. Roof in *Tetrahedron Lett.*, 2747 (1967).

The method used for preparing the intermediate sulfonamides when R is $SO_2NR_6R_7$ is included in Equations 6a-d.

Equations 6a-d

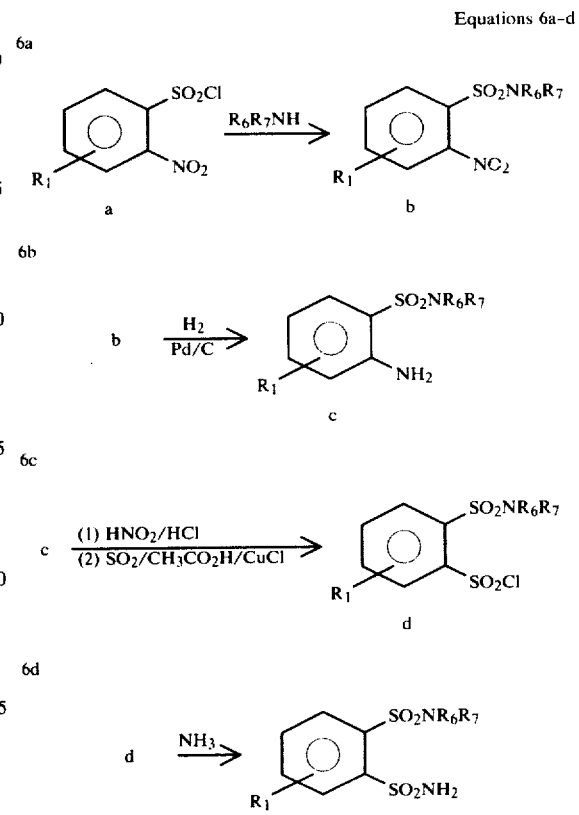

wherein
$R_1$, $R_6$ and $R_7$ are as previously defined.

In step (6a), the o-nitrobenzenesulfonyl chlorides in Formula a, which are well-known in the art, are treated with an amine, $R_6R_7NH$, in an inert organic solvent such as methylene chloride, ethyl ether, or tetrahydrofuran at 0°-50° C. The amine may be taken in excess to act as an acid acceptor; alternatively, a tertiary amine such as triethylamine or pyridine may be used as an acid acceptor. The by-product amine hydrochloride is filtered off or washed out of the solvent with water and the product isolated by evaporation of the solvent.

The reduction described in step (6b) is accomplished by treating a solution of the compounds of Formula b in a solvent such as ethanol, ethyl acetate, or DMF, in a pressure vessel with 100-1000 pounds per square inch of hydrogen at 80°-150° C. in the presence of a hydrogenation catalyst such as 5-10% palladium absorbed on carbon. When the theoretical amount of hydrogen has been absorbed, the solution is cooled and the catalyst is removed by filtration. The product is then isolated by evaporation of the solvent.

The diazotization and coupling with sulfur dioxide, described in step (6c) is accomplished in the following manner. A solution of the sulfamoyl compound of Formula c in a mixture of concentrated hydrochloric acid and glacial acetic acid is treated with a solution of sodium nitrite in water at −5° to 0° C. After stirring for 10–15 minutes at 0° C. to insure complete diazotization, this solution is added to a mixture of an excess of sulfur dioxide and a catalytic amount of cuprous chloride in glacial acetic acid at 0°–5° C. The temperature is kept at 0°–5° C. for ¼ to 1 hour and is then raised to 20°–25° C. and held at that temperature for 2–4 hours. This solution is then poured into a large excess of ice-water. The sulfonyl chloride products, d, can be isolated by filtration or by extraction into solvent such as ethyl ether or methylene chloride followed by evaporation of the solvent.

The amination described in step (6d) is conveniently carried out by treating a solution of the sulfonyl chloride of Formula d with an excess of anhydrous ammonia in a solvent such as ethyl ether or methylene chloride at 0°–25° C. If the product sulfonamide is insoluble it may be isolated by filtration followed by washing out the salts with water. If the product sulfonamide is soluble in the reaction solution, it may be isolated by filtering off the precipitated ammonium chloride and evaporating the solvent.

The sulfonamide precursors to intermediates of Formula IV in which R is $SO_2OCH_2CF_3$, $SO_2OCH_2CCl_3$ or $SO_2N(CH_3)OCH_3$ can be prepared through a sequence analogous to that shown in Equations 6a–d. In step 6a, the amine is replaced by the appropriate alkoxide salt or N-methoxy-N-methylamine and the resulting nitro compound is treated as in Equations 6b–d.

Equation 7 describes the preparation of intermediate sulfonamides of Formula VIII when R is $SO_2R_5$.

Equations 7a–c

7a

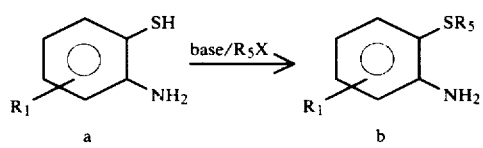

7b

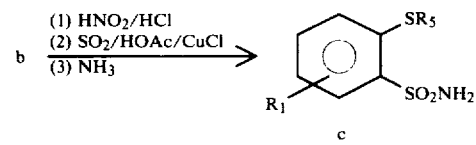

7c

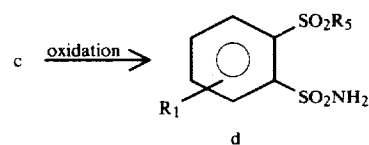

wherein $R_1$ and $R_5$ are as previously defined.

The thioether of Equation 7a may be prepared from the appropriate 2-aminothiophenol and an alkyl halide as described in the literature, e.g., R. N. Prasad et al., Can. J. Chem. 44, 1247 (1966). The formation of the sulfonamide c is analogous to that presented in Equations 6c and 6d above.

The oxidation of c to the corresponding 2-alkylsulfonylbenzenesulfonamides of Equation 7c may be carried out utilizing any of several of standard literature procedures with m-chloroperbenzoic acid (C. R. Johnson, et al., Tetradedron. 25, 5649 (1969)), or with aqueous hydrogen peroxide in acetic acid (F. G. Bordwell, et al., J. Amer. Chem. Soc. 77, 1141, (1955).

The intermediate sulfonyl chlorides and the sulfonamides VIII in which R is $CH_2P$ (wherein P is as previously defined) may be synthesized from the corresponding nitrobenzenes by reduction, then diazotization in the presence of sulfur dioxide and cuprous chloride as shown above.

The o-alkoxymethyl- or o-alkylsulfonylmethylnitrobenzenes are in turn prepared via "Williamson Synthesis", according to Equations 8a or 8b.

Equations 8a-b

8a

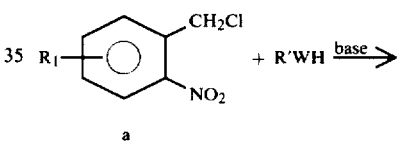

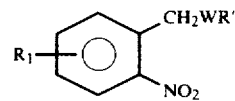

8b

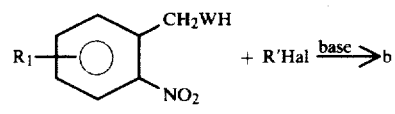

W = O or S;
R' = $C_1-C_4$ alkyl or $C_3-C_4$ alkenyl.

"Williamson Synthesis" has been widely used for the preparation of ethers as reviewed by W. Theilheimer, Syn. Methods of Org. Chem., Vol. VII, p. 112. The thioethers formed in Equations 8a or b (W=S) may then be oxidized to the corresponding sulfones in a manner similar to that described in Equation 7c.

Benzenesulfonamides of Formula X can also be derived from compound IX as illustrated in Equation 8c.

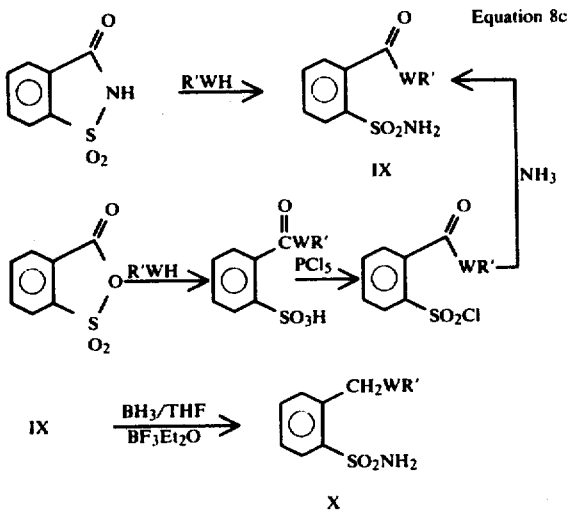

Equation 8c

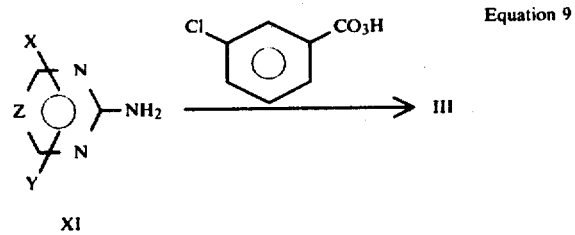

Preparation of o-sulfamylbenzoic acid esters, IX, from saccharin or sulfobenzoic acid anhydride is well-known in the art, e.g., B. Loev and M. Kormendy, *J. Org. Chem.* 27, 1703 (1962). The esters, IX, can be readily reduced to the ethers, X, with diborane in a suitable organic solvent, e.g., tetrahydrofuran, in the presence of fifteen fold excess of boron trifluoride etherate under reflux for 18 hours, as described by R. P. Graber and M. B. Meyers, *J. Org. Chem.* 26, 4773 (1961).

The compounds of this invention in which R is an ortho sulfonate derivative ($OSO_2R_9$) may also be prepared via the corresponding sulfonamides of Formula VIII. These intermediates may be prepared as described in "Research Disclosure", p. 52, (1978).

B. Aminoheterocyclic-N-Oxide Intermediates

The aminoheterocyclic-N-oxides of Formula III can be prepared as shown below in Equation 9 by the reaction of an appropriately substituted aminoheterocycle XI with an oxidizing agent such as m-chloroperoxybenzoic acid.

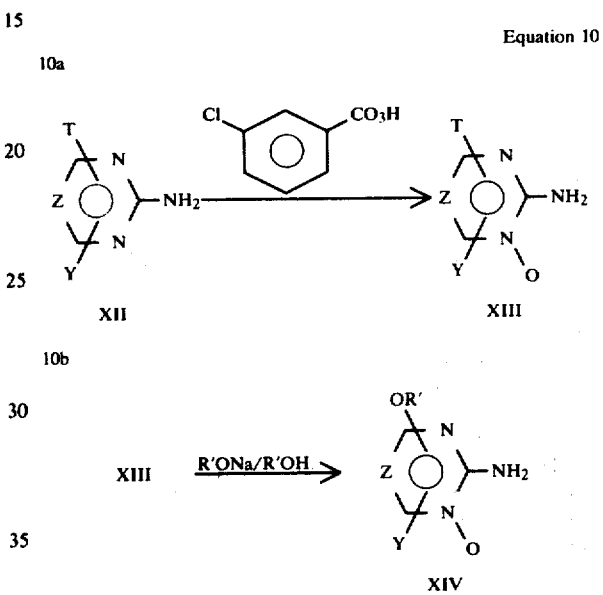

Equation 9 wherein
X, Y and Z are as previously defined.

As shown in Equation 9, an aminoheterocycle is reacted with an oxidizing agent such as m-chloroperoxybenzoic acid in aprotic solvent such as acetone, methylethylketone, methylene chloride or chloroform. Temperatures of 20°–80° C. over 2–15 hours are usually required to complete the reaction. The products are isolated by cooling and filtration. Alternatively, if the aminoheterocyclic-N-oxides III are soluble in the solvents chosen, they may be isolated by stirring the reaction mixture with potassium carbonate or sodium carbonbate, filtration and concentration of the filtrate. The crude aminoheterocyclic-N-oxides III may be purified by washing with solvents such as acetone, ether or ethyl acetate. In cases that X and Y are different, there may be two isomeric compounds of Formula III formed. The two N-oxide isomers may be separated, for example, by column chromatography and reacted as in Equation 2 or they may be used as a mixture in this reaction to give the corresponding isomeric mixture of two products which is also useful for practicing this invention.

The compounds of Formula III may also be prepared from aminoheterocycles XIII by the sequence of reactions described in Equation 10.

Equation 10 wherein
Y and Z are as previously defined; and
R' is $CH_3$ or $CH_3CH_2$ and T is Cl or Br.

The reaction of Equation 10a is best carried out in an aprotic solvent such as acetone, methylethylketone, methylene chloride or chloroform. Temperatures of 20°–80° C. over 2–15 hours are usually required to complete the reaction. The product XIII are isolated by cooling and filtration. Alternatively, if the aminoheterocyclic-N-oxides XIII are soluble in the solvent chosen, they may be isolated by stirring the reaction mixture with potassium carbonate or sodium carbonate, filtration and concentration of the filtrate. The crude aminoheterocyclic-N-oxides XIII may be purified by washing with solvents such as acetone, ether or ethyl acetate.

Displacement of the halogen T of compound XIII may be accomplished as shown in Equation 10b by treatment of the aminoheterocyclic-N-oxides XIII with a solution of an alkali metal alkoxide in the corresponding alcohol, such as sodium methoxide in methanol. Temperatures of 40°–78° C. over 2 to 20 hours are usually required to complete the reaction. The product XIV may be isolated by filtration, acidification of the filtrate and evaporation of the solvent. Purification of the products XIV may be accomplished by refluxing the crude residue in solvents such as ethyl acetate or acetone followed by cooling and collecting the resulting solid products by filtration.

The synthesis of heterocyclic amines has been reviewed in "The Chemistry of Heterocyclic Compounds", published by Interscience Publ., New York and London. 2-Aminopyrimidines are described by D. J. Brown in Vol. XVI of this series. The 2-amino-1,3,5-triazines are reviewed by K. R. Huffman and in "The Triazines" of this same series. The synthesis of triazines is also described by F. C. Schaefer, U.S. Pat. No. 3,154,547 and by K. R. Huffman and F. C. Schaeffer, *J. Org. Chem.* 28, 1816 (1963).

C. Fused [1,2,4]oxadiazolo[2,3-a]heterocyclicimine hydrobromide intermediates Many of the intermediate fused [1,2,4]oxadiazolo[2,3-a]heterocyclicimine hydrobromides of Formula II can be prepared by reacting an aminoheterocyclic-N-oxide of Formula III with cyanogen bromide, as shown in Equation 11.

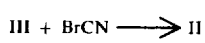

Equation 11 wherein

X, Y and Z are as previously defined.

The reaction of Equation 11 is best carried out in protic organic solvents such as ethanol or methanol at 25°–80° C. over 1–8 hours. The mode of addition is not critical; however, it is often convenient to add cyanogen bromide to a solution of the aminoheterocyclic-N-oxide. The desired product is isolated by evaporation of solvents, trituration of the residue with a solvent such as methylene chloride or ether and filtration.

Agriculturally suitable salts of compounds of Formula I are also useful herbicides. Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

4,6-Dimethyl-1-oxide-2-pyrimidinamine

A solution of 24.0 g of m-chloroperoxybenzoic acid in 200 ml of acetone was added to a solution of 13.0 g of 4,6-dimethyl-2-pyrimidinamine in 300 ml of acetone with stirring. The mixture was stirred at room temperature for about two hours. The precipitate was then collected by filtration, washed with acetone and dried to yield 11.0 g of 4,6-dimethyl-1-oxide-2-pyrimidinamine, m.p. 252° C. (dec.).

NMR (DMSO-d$_6$)δ: 2.2 (s, 3H); 2.3 (s, 3H); 6.7 (s, 1H); 7.53 (b, 2H) ppm.

EXAMPLE 2

4-Chloro-6-methyl-1-oxide-2-pyrimidinamine

A solution of 28.0 g of m-chloroperoxybenzoic acid in 200 ml of acetone was added to a solution of 17.3 g of 4-chloro-6-methyl-2-pyrimidinamine in 500 ml of acetone with stirring. The mixture was stirred at room temperature overnight. The precipitate was then collected by filtration, washed with acetone and dried to yield 13.0 g of 4-chloro-2-methyl-1-oxide-2-pyrimidinamine, m.p. 155° C. (dec.).

NMR (DMSO-d$_6$)δ: 2.35 (s, 3H); 6.95 (s, 1H); 8.06 (b, 2H) ppm.

EXAMPLE 3

4-Methoxy-6-methyl-1-oxide-2-pyrimidinamine

A solution of 11.2 g of 4-chloro-6-methyl-1-oxide-2-pyrimidinamine and 5.4 g of sodium methoxide in 200 ml of methanol was refluxed for 12 hours. The reaction mixture was then cooled down to room temperature and was filtered. The filtrate was acidified with concentrated hydrogen chloride solution to pH 7. The filtrate was then evaporated to dryness. The residue was washed with ether, boiling ethyl acetate and then ether. The solid collected was dried to yield 10.0 g of 4-methoxy-6-methyl-1-oxide-2-pyrimidinamine, m.p. 199°–201° C.

NMR (TFA)δ: 2.53 (s, 3H); 4.02 (s, 3H); 6.3 (s, 1H); 6.9 (b, 2H) ppm.

EXAMPLE 4

Dimethyl N-(2-chlorophenylsulfonyl)carbonimidodithioate

To a stirred solution of 28.75 g of 2-chlorobenzenesulfonamide in 75 ml of dimethylformamide at ambient temperature was added 8.45 g of potassium hydroxide and 4.55 ml of carbon disulfide. The mixture was stirred at ambient temperature for 2 hours. To this mixture was then added another 8.45 g of potassium hydroxide and 4.55 ml of carbon disulfide. The mixture was stirred at ambient temperature for another 2 hours and then cooled to about 5° C. To this mixture was added 23.0 g of methyl iodide. Another 23 g of methyl iodide was then added at ambient temperature. The mixture was stirred at ambient temperature for two hours and then added to 1 liter of chilled water. The precipitate was collected by filtration, and dried to yield 20.0 g of dimethyl N-(2-chlorophenylsulfonyl)carbonimidodithioate, m.p. 119°–123° C.

NMR (DMSO-d$_6$)δ: 2.6 (s, 6H); 7.5–8.4 (m, 4H) ppm.

EXAMPLE 5

2-Chloro-N-[5,7-dimethyl-2H-[(1,2,4)oxadiazolo(2,3-a)pyrimidin-2-ylidene]benzenesulfonamide To a dry stirred solution of 2.0 g of dimethyl-N-(2-chlorophenylsulfonyl)carbonimidodithioate in 10 ml of methylene chloride at ambient temperature was added 3.0 g of sulfuryl chloride. The resulting mixture was stirred at ambient temperature overnight and then refluxed for another 3 hours. The mixture was cooled down to room temperature and 2.0 g of sulfuryl chloride was added. The mixture was stirred at room temperature for an additional 2 days. The solvent was evaporated under reduced pressure. To the stirred residue oil was added a suspension of 1.0 g of 4,6-dimethyl-1-oxide-2-pyrimidinamine in 30 ml of anhydrous tetrahydrofuran. To the above mixture was added 0.54 g of 60% sodium hydride in portions at ambient temperature. The mixture was stirred at room temperature for 2 days, then concentrated to half of the original volume under reduced pressure and added to 250 ml of distilled water. The precipitate was collected by filtration, washed with ether and dried to yield 0.7 g of 2-chloro-N-[5,7-dimethyl-2H-[(1,2,4)oxadiazolo(2,3-a)pyrimidin-2-ylidene]]benzenesulfonamide, m.p. 185°–186° C. (dec.).

NMR (DMSO-d$_6$)δ: 2.5 (d, 6H); 7.2 (s, 1H); 7.3–8.3 (m, 4H) ppm.

EXAMPLE 6

2-Chloro-N-[5-methoxy-7-methyl-2H-[(1,2,4)oxadiazolo(2,3-a)pyrimidin-2-ylidene]]benzenesulfonamide To a stirred solution of 2.0 g of dimethyl-N-(2-chlorophenylsulfonyl)carbonimidodithioate in 10 ml of anhydrous methylene chloride at ambient temperature was added 4.0 g of sulfuryl chloride. The mixture was stirred at room temperature for 2 days. To this mixture at ambient temperature was added another 1.4 g of sulfuryl chloride, and the mixture was stirred at room temperature for another day. The solvent was evaporated under reduced pressure. To the stirred residue oil was added a suspension of 1.1 g of 4-methoxy-6-methyl-1-oxide-2-pyrimidinamine in 30 ml of anhydrous tetrahydrofuran. To this mixture was added 0.54 g of 60% sodium hydride in portions. The mixture was stirred at room temperature for 2 days then concentrated to half of the original volume under reduced pressure and added to 250 ml of distilled water. The precipitate was collected by filtration, washed with ether and dried to yield 1.2 g of 2-chloro-N-[5-methoxy-7-methyl-2H-[(1,2,4)oxadiazolo(2,3-a)pyrimidin-2-ylidene]]benzenesulfonamide, m.p. 178° C. (dec.).

NMR (DMSO-$d_6$)$\delta$: 2.53 (s, 3H); 3.97 (s, 3H); 6.8 (s, 1H); 7.3–8.3 (m, 4H) ppm.

EXAMPLE 7

5,7-Dimethyl-2H-[1,2,4]oxadiazolo[2,3-a]pyrimidine-2-imine hydrobromide

To a stirred solution of 14.0 g of 4,6-dimethyl-1-oxide-2-pyrimidinamine in 200 ml of absolute ethanol at ambient temperature and pressure was added 16.0 g of cyanogen bromide. The mixture was refluxed for 1 hour. Charcoal was then added, and the mixture was refluxed for another 10 minutes and then filtered. The filtrate was concentrated under reduced pressure. The residue oil was triturated with ether followed by methylene chloride. The solid crystallized was collected by filtration, washed with methylene chloride and dried to yield 12 g of 5,7-dimethyl-2H-[2,3,4]oxadiazolo[2,3-a]pyrimidine-2-imine hydrobromide, m.p. 153°–154° C. (dec.).

IR (cm$^{-1}$): 1700 cm$^{-1}$.

EXAMPLE 8

2-Nitro-N-[5,7-dimethyl-2H-[(1,2,4)oxadiazolo(2,3-a)pyrimidin-2-ylidene]]benzenesulfonamide To a stirred suspension of 1.6 g of 5,7-dimethyl-2H-[1,2,4]oxadiazolo[2,3-a]pyrimidine-2-imine hydrobromide and 1.4 g of o-nitrobenzenesulfonyl chloride in 60 ml of anhydrous methylene chloride at 0° C. is added a solution of 1.0 g of triethylamine in 10 ml of anhydrous methylene chloride dropwise. After addition, the mixture is stirred at 0° C. for 0.5 hour and then at ambient temperature for 2.5 hours. The mixture is then filtered. The filtrate is concentrated under reduced pressure and then column chromatographied (silica gel) to yield 2-nitro-N-[5,7-dimethyl-2H-[1,2,4)oxadiazolo(2,3-a)pyrimidin-2-ylidene]]benzenesulfonamide.

EXAMPLE 9

Dimethyl, N-[[2-[(Dimethylamino)sulfonyl]phenyl]sulfonyl]carbonimidodithioate

To a dry stirred solution of 0.9 g of N,N-dimethyl-1,2-benzenedisulfonamide in 25 ml of acetonitrile at ambient temperature was added 2.0 g of tri(methylthio)methyltetrafluoroborate and then 0.9 g of 2,6-lutidine. This mixture was heated at 60° C. for 3 days. The mixture was cooled down to room temperature and was evaporated under reduced pressure to dryness. The residue was then column chromatographed [silica gel, ethyl acetate/methylene chloride (1/10)] to yield 1.08 g of dimethyl, N-[[2-[(dimethylamino)sulfonyl]phenyl]sulfonyl]carbonimidodithioate, m.p. 150°–153° C.

NMR (DMSO-$d_6$)$\delta$: 2.53 (s, 6H); 2.8 (s, 6H); 7.6–8.46 (m, 4H).

EXAMPLE 10

N,N-Dimethyl-N'-(5,7-dimethyl-2H-1,2,4-oxadiazolo[2,3-A]-pyrimidin-2-ylidene)-1,2-benzenedisulfonamide To a dry stirred solution of 1.8 g of dimethyl, N-[[2-[(dimethylamino)sulfonyl]phenyl]sulfonyl]carbonimidodithioate in 10 ml of methylene chloride at ambient temperature was added 4 g of sulfuryl chloride. This mixture was stirred at room temperature for 2 days. To this solution is then added 1 ml of additional sulfuryl chloride. The mixture was stirred at ambient temperature for an additional 24 hours and was then evaporated under reduced pressure. To the residue oil was added a dry stirred suspension of 0.75 g of 4,6-dimethyl-1-oxide-2-pyrimidinamine in 22 ml of tetrahydrofuran. To this stirred mixture at ambient temperature was then added 0.4 g of 60% sodium hydride portionwise. This mixture was then stirred at room temperature for 2 days. The mixture was then concentrated to half of its original volume under reduced pressure and was poured into 200 ml of ice-water. The solid precipitate was filtered, washed with ether and dried in an oven to yield 1.0 g of N,N-dimethyl-N'-(5,7-dimethyl-2H-1,2,4-oxadiazolo[2,3-A]-pyrimidin-2-ylidene)-1,2-benzenedisulfonamide, m.p. 123°–125° C. (dec.).

NMR (DMSO-$d_6$)$\delta$: 2.5 (s, 3H); 2.6 (s, 3H); 2.8 (s, 6H); 7.25 (s, 1H); 7.66–8.53 (m, 4H).

By application of one or more of the procedures of Examples 1 through 10 and/or the general procedures described above, the compounds of Tables I and II can be prepared.

TABLE Ia

| R | $R_1$ | X | Y | m.p. (°C.) |
|---|---|---|---|---|
| $CH_3$ | H | $CH_3$ | $CH_3$ | |
| $C_2H_5$ | H | $CH_3$ | $OCH_3$ | |
| $CH_3$ | 5-Cl | $OCH_3$ | $CH_3$ | |

TABLE Ia-continued

| R | R₁ | X | Y | m.p. (°C.) |
|---|---|---|---|---|
| CH₂CH₂CH₃ | H | OCH₃ | OCH₃ | |
| CH(CH₃)₂ | H | CH₃ | CH₃ | |
| C(CH₃)₂ | H | OCH₃ | OCH₃ | |
| CH₃ | 5-NO₂ | CH₃ | OCH₃ | |
| CH₃ | 5-CH₃ | OCH₃ | OCH₃ | |
| OCH₃ | H | CH₃ | CH₃ | |
| OCH₃ | H | CH₃ | OCH₃ | |
| OC₂H₅ | H | OCH₃ | CH₃ | |
| OCH(CH₃)₂ | H | OCH₃ | OCH₃ | |
| OC(CH₃)₃ | H | OCH₃ | CH₃ | |
| OCH(CH₃)C₂H₅ | 3-F | CH₃ | OCH₃ | |
| OCH₃ | 6-Br | OCH₃ | OCH₃ | |
| Cl | H | CH₃ | CH₃ | 185–186° |
| Cl | H | CH₃ | OCH₃ | 178° (dec) |
| Cl | H | OCH₃ | CH₃ | |
| Cl | H | OCH₃ | OCH₃ | |
| Cl | 6-CH₃ | CH₃ | C₂H₅ | |
| Cl | H | OCH₃ | CH₂OC₂H₅ | |
| Cl | 5-NO₂ | C₂H₅ | OC₂H₅ | |
| Cl | H | CH₃ | OC₂H₅ | 80° (d) |
| Br | H | CH₃ | CH₃ | |
| Br | H | OCH₃ | OCH₃ | |
| F | H | OCH₃ | CH₃ | |
| F | H | CH₃ | OCH₃ | |
| CF₃ | H | CH₃ | CH₃ | |
| CF₃ | H | OCH₃ | OCH₃ | |
| CF₃ | H | OC₂H₅ | CH₃ | |
| CF₃ | H | CH₃ | CF₃ | |
| NO₂ | H | CH₃ | H | |
| NO₂ | H | CH₃ | OCH₃ | |
| NO₂ | H | OCH₃ | CH₂CH₂OC₂H₅ | |
| NO₂ | 6-Cl | OCH₃ | OCH₃ | |
| NO₂ | H | OC₂H₅ | CH₂CH₂OCH₃ | |
| CO₂CH₃ | H | OCH₃ | OCH₃ | |
| CO₂CH₃ | H | CH₃ | CH₃ | |
| CO₂CH₃ | H | OCH₃ | CH₃ | |
| CO₂CH₃ | H | CH₃ | OCH₃ | |
| CO₂CH₃ | H | CH₃ | H | |
| CO₂CH₃ | H | OCH₃ | O(CH₂)₃CH₃ | |
| CO₂CH₃ | H | CH₃ | OCH(CH₃)₂ | |
| CO₂C₂H₅ | H | CH₃ | CH₃ | |
| CO₂CH(CH₃)₂ | H | OC₂H₅ | OCH₃ | |
| CO₂(CH₂)₃CH₃ | H | CH₃ | OCH₃ | |
| CO₂CH(CH₃)C₂H₅ | H | CH₃ | CH₃ | |
| CO₂(CH₂)₅CH₃ | H | OCH₃ | CH₃ | |
| CO₂CH₂CH=CH₂ | H | CH₃ | Cl | |
| CO₂CH₂CH=CH₂ | H | CH₃ | OCH₃ | |
| CO₂CH₂CH=CHCH₃ | H | OCH₃ | OCH₃ | |
| CO₂(CH₂)₄CH=CH₂ | H | CH₃ | CH₃ | |
| CO₂CH₂CF₃ | H | OCH₃ | OCH₃ | |
| CO₂CH₂CH₂Cl | H | OCH₃ | CH₃ | |
| CO₂(CH₂)₃Br | H | OCH₃ | OCH₃ | |
| CO₂(CH₂)₄CHBrCH₂Br | H | CH₃ | CH₃ | |
| CO₂CH(CF₃)CH₃ | H | CH₃ | OCH₃ | |
| CO₂CH₂CCl₃ | H | CH₃ | Cl | |
| CO₂-cyclopentyl | H | CH₃ | CH₃ | |
| CO₂-cyclohexyl | H | OCH₃ | OCH₃ | |
| CO₂CH₂CH₂OCH₃ | H | CH₃ | H | |
| CO₂(CH₂CH₂O)₂CH₃ | H | CH₃ | CH₃ | |
| CO₂(CH₂CH₂O)₂C₂H₅ | H | CH₃ | OCH₃ | |
| CO₂CH₂CH₂OC₂H₅ | H | OCH₃ | CH₃ | |
| CO₂(CH₂)₃OCH₃ | H | OCH₃ | OCH₃ | |
| CO₂(CH₂)₃OC₂H₅ | H | CH₃ | CH₃ | |

TABLE 1a-continued

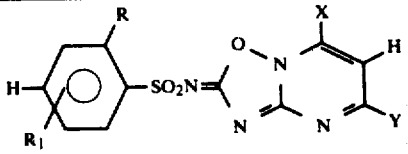

| R | R₁ | X | Y | m.p. (°C.) |
|---|---|---|---|---|
| $SO_2CH_3$ | H | $CH_3$ | $CH_3$ | |
| $SO_2CH_3$ | H | $OCH_3$ | $CH_3$ | |
| $SO_2CH_3$ | H | $CH_3$ | $OCH_3$ | |
| $SO_2CH_3$ | H | $OCH_3$ | $CH(CH_3)_2$ | |
| $SO_2C_2H_5$ | H | $C_2H_5$ | $C_2H_5$ | |
| $SO_2CH(CH_3)_2$ | H | $CH_3$ | $OCH_3$ | |
| $SO_2(CH_2)_2CH_3$ | H | $OCH_3$ | $CH_3$ | |
| $SO_2(CH_2)_3CH_3$ | H | $OCH_3$ | $OCH_3$ | |
| $SO_2CH(CH_3)C_2H_5$ | H | $CH_3$ | $CH_3$ | |
| $SO_2OCH_2CF_3$ | H | $OCH_3$ | $CH_3$ | |
| $SO_2OCH_2CCl_3$ | H | $CH_3$ | $OCH_3$ | |
| $SO_2N(OCH_3)CH_3$ | H | $CH_3$ | $OC_2H_5$ | |
| $SO_2N(CH_3)_2$ | H | $CH_3$ | $CH_3$ | 123–125° (dec) |
| $SO_2N(CH_3)_2$ | H | $CH_3$ | $OCH_3$ | 235–236° |
| $SO_2N(CH_3)_2$ | H | $OCH_3$ | $CH_3$ | |
| $SO_2N(CH_3)C_2H_5$ | H | $OCH_3$ | $CH_2OCH_3$ | |
| $SO_2N(C_2H_5)_2$ | H | $OCH_3$ | $OCH_3$ | |
| $SO_2N(CH_3)(CH_2)_3CH_3$ | H | $CH_3$ | $CH_3$ | |
| $SO_2N[CH(CH_3)_2]CH_3$ | H | $CH_3$ | $OCH_3$ | |
| $SO_2N(CH_3)_2$ | H | $OCH_3$ | $(CH_2)_3CH_3$ | |
| $OCHF_2$ | H | $OCH_3$ | $OCH_3$ | |
| $OCF_3$ | H | $CH_3$ | $CH_3$ | |
| $OCH_2CF_3$ | H | $CH_3$ | $CF_3$ | |
| $OCF_2CHF_2$ | H | $CH_3$ | $Cl$ | |
| $OCF_2CHFCl$ | H | $CH_3$ | $OCH_3$ | |
| $OCF_2CHFBr$ | H | $OCH_3$ | $CH_3$ | |
| $OCF_2CHFCF_3$ | H | $OC_2H_5$ | $OC_2H_5$ | |
| $SO_2CHF_2$ | H | $CH_3$ | $CH_3$ | |
| $SO_2CH_2CF_3$ | H | $CH_3$ | $OCH_3$ | |
| $SO_2CF_3$ | H | $OCH_3$ | $CH_3$ | |
| $SO_2CF_2CHF_2$ | H | $OCH_3$ | $OCH_3$ | |
| $SO_2CF_2CHFCF_3$ | H | $CH_3$ | $CH_3$ | |
| $OSO_2CH_3$ | H | $CH_3$ | $OCH_3$ | |
| $OSO_2CH_3$ | H | $CH_3$ | $CH_3$ | |
| $OSO_2C_2H_5$ | H | $CH_3$ | $OCH_3$ | |
| $OSO_2(CH_2)_2CH_3$ | H | $OCH_3$ | $CH_3$ | |
| $OSO_2(CH_2)_3CH_3$ | H | $OCH_3$ | $OCH_3$ | |
| $OSO_2CH_2Cl_2Cl$ | H | $OCH_3$ | $CH_3$ | |
| $OSO_2CF_3$ | H | $CH_3$ | $CH_3$ | |
| $OSO_2CH_2CCl_3$ | H | $OCH_3$ | $H$ | |
| $OSO_2CH_2CH_2CH_2Br$ | H | $OCH_3$ | $CH_3$ | |
| $CH_2OCH_3$ | H | $CH_3$ | $CH_3$ | |
| $CH_2OC_2H_5$ | H | $CH_3$ | $OCH_3$ | |
| $CH_2O(CH_2)_2CH_3$ | H | $OCH_3$ | $CH_3$ | |
| $CH_2OC(CH_3)_3$ | H | $OCH_3$ | $OCH_3$ | |
| $CH_2OCH(CH_3)_2$ | H | $CH_3$ | $CH_3$ | |
| $CH_2OCH_3$ | $3\text{-}OCH_3$ | $OCH_3$ | $CH_3$ | |
| $CH_2OCH_3$ | H | $CH_3$ | $OC_2H_5$ | |
| $CH_2OCH_2CH=CH_2$ | H | $CH_3$ | $OCH_3$ | |
| $CH_2OCH_2CH=CHCH_3$ | H | $CH_3$ | $CH_3$ | |
| $CH_2OCH_2C(CH_3)=CH_2$ | H | $OCH_3$ | $OCH_3$ | |
| $CH_2SO_2CH_3$ | H | $CH_3$ | $CH_3$ | |
| $CH_2SO_2CH_2CH_3$ | H | $OCH_3$ | $OCH(CH_3)_2$ | |
| $CH_2SO_2CH_3$ | H | $CH_3$ | $O(CH_2)_3CH_3$ | |
| $CH_2SO_2CH(CH_3)_2$ | H | $OCH_3$ | $OCH_3$ | |
| $CH_2SO_2(CH_2)_3CH_3$ | H | $CH_3$ | $OCH_3$ | |
| $CH_2SO_2CH_3$ | H | $OC_2H_5$ | $CH_3$ | |
| $CH_2SO_2(CH_2)_2CH_3$ | H | $C_2H_5$ | $OCH_3$ | |
| $CH_2OC_2H_5$ | $5\text{-}OCH_3$ | $CH_3$ | $CH_3$ | |
| Cl | $5\text{-}C_2H_5$ | $CH_3$ | $CH_3$ | |
| $CH_3$ | $5\text{-}CH(CH_3)_2$ | $CH_3$ | $OCH_3$ | |
| $OCH_3$ | $5\text{-}(CH_2)_3CH_3$ | $CH_3$ | $OCH_3$ | |
| Br | $3\text{-}O(CH_2)_2CH_3$ | $OCH_3$ | $OCH_3$ | |
| F | $5\text{-}CF_3$ | $OCH_3$ | $CH_3$ | |
| $CO_2CH_3$ | $5\text{-}OC(CH_3)_3$ | $CH_3$ | $CH_3$ | |
| $CO_2CH_3$ | $5\text{-}NO_2$ | $CH_3$ | $OCH_3$ | |
| $SO_2N(CH_3)_2$ | H | $CH_3$ | $OC_2H_5$ | 108–110° (d) |

TABLE Ib

| R | R₁ | X | Y | m.p.(°C.) |
|---|---|---|---|---|
| Cl | H | OCH₃ | CH₂OC₂H₅ | |
| CF₃ | H | CH₃ | CF₃ | |
| NO₂ | H | OCH₃ | CH₂CH₂OC₂H₅ | |
| NO₂ | H | OC₂H₅ | CH₂CH₂OCH₃ | |
| CO₂CH₃ | H | OCH₃ | O(CH₂)₃CH₃ | |
| CO₂CH₃ | H | CH₃ | OCH(CH₃)₂ | |
| CO₂CH₂CH₂OCH₃ | H | CH₃ | H | |
| SO₂CH₃ | H | OCH₃ | CH(CH₃)₂ | |

TABLE Ib-continued

| R | R₁ | X | Y | m.p. (°C.) |
|---|---|---|---|---|
| SO₂N(CH₃)C₂H₅ | H | OCH₃ | CH₂OCH₃ | |
| SO₂N(CH₃)₂ | H | OCH₃ | (CH₂)₃CH₃ | |
| OCH₂CF₃ | H | CH₃ | CF₃ | |
| OSO₂CH₂CCl₃ | H | OCH₃ | H | |
| CH₂OCH₃ | H | OCH₃ | OC₂H₅ | |
| CH₂SO₂CH₃ | H | CH₃ | O(CH₂)₂CH₃ | |
| CO₂CH₃ | H | CH₃ | H | |

TABLE IIa

| R | R₁ | X | Y | m.p. (°C.) |
|---|---|---|---|---|
| CH₃ | H | CH₃ | CH₃ | |
| C₂H₅ | H | CH₃ | OCH₃ | |
| CH₃ | 5-Cl | OCH₃ | CH₃ | |
| CH₂CH₂CH₃ | H | OCH₃ | OCH₃ | |
| CH(CH₃)₂ | H | CH₃ | CH₃ | |
| C(CH₃)₃ | H | OCH₃ | CH₃ | |
| CH₃ | 5-NO₂ | CH₃ | OCH₃ | |
| CH₃ | 5-CH₃ | OCH₃ | OCH₃ | |
| OCH₃ | H | CH₃ | CH₃ | |
| OCH₃ | H | CH₃ | OCH₃ | |
| OC₂H₅ | H | OCH₃ | CH₃ | |
| OCH(CH₃)₂ | H | OCH₃ | OCH₃ | |
| OC(CH₃)₃ | H | OCH₃ | CH₃ | |
| OCH(CH₃)C₂H₅ | 3-F | CH₃ | OCH₃ | |
| OCH₃ | 6-Br | OCH₃ | OCH₃ | |
| Cl | H | CH₃ | CH₃ | |
| Cl | H | CH₃ | OCH₃ | |
| Cl | H | OCH₃ | CH₃ | |
| Cl | H | OCH₃ | OCH₃ | |
| Cl | 6-CH₃ | CH₃ | C₂H₅ | |
| Cl | H | OCH₃ | CH₂OC₂H₅ | |
| Cl | 5-NO₂ | C₂H₅ | OC₂H₅ | |
| Cl | H | CH₃ | OC₂H₅ | |
| Br | H | CH₃ | CH₃ | |
| Br | H | OCH₃ | OCH₃ | |
| F | H | OCH₃ | CH₃ | |
| F | H | CH₃ | OCH₃ | |
| CF₃ | H | CH₃ | CH₃ | |
| CF₃ | H | OCH₃ | OCH₃ | |
| CF₃ | H | OC₂H₅ | CH₃ | |
| CF₃ | H | CH₃ | CF₃ | |
| NO₂ | H | CH₃ | H | |
| NO₂ | H | CH₃ | OCH₃ | |
| NO₂ | H | OCH₃ | CH₂CH₂OC₂H₅ | |
| NO₂ | 6-Cl | OCH₃ | OCH₃ | |
| NO₂ | H | OC₂H₅ | CH₂CH₂OCH₃ | |
| CO₂CH₃ | H | OCH₃ | OCH₃ | |
| CO₂CH₃ | H | CH₃ | CH₃ | |
| CO₂CH₃ | H | OCH₃ | CH₃ | |
| CO₂CH₃ | H | CH₃ | OCH₃ | |
| CO₂CH₃ | H | CH₃ | H | |
| CO₂CH₃ | H | OCH₃ | O(CH₂)₃CH₃ | |
| CO₂CH₃ | H | CH₃ | OCH(CH₃)₂ | |
| CO₂C₂H₅ | H | CH₃ | CH₃ | |
| CO₂CH(CH₃)₂ | H | OC₂H₅ | OCH₃ | |
| CO₂(CH₂)₃CH₃ | H | CH₃ | OCH₃ | |
| CO₂CH(CH₃)C₂H₅ | H | CH₃ | CH₃ | |
| CO₂(CH₂)₅CH₃ | H | OCH₃ | CH₃ | |
| CO₂CH₂CH=CH₂ | H | CH₃ | Cl | |
| CO₂CH₂CH=CH₂ | H | CH₃ | OCH₃ | |
| CO₂CH₂CH=CHCH₃ | H | OCH₃ | OCH₃ | |
| CO₂(CH₂)₄CH=CH₂ | H | CH₃ | CH₃ | |
| CO₂CH₂CF₃ | H | OCH₃ | OCH₃ | |
| CO₂CH₂CH₂Cl | H | OCH₃ | CH₃ | |

TABLE IIa-continued

| R | R₁ | X | Y | m.p. (°C.) |
|---|---|---|---|---|
| CO$_2$(CH$_2$)$_3$Br | H | CH$_3$ | OCH$_3$ | |
| CO$_2$(CH$_2$)$_4$CHBrCH$_2$Br | H | CH$_3$ | CH$_3$ | |
| CO$_2$CH(CF$_3$)CH$_3$ | H | CH$_3$ | OCH$_3$ | |
| CO$_2$CH$_2$CCl$_3$ | H | CH$_3$ | Cl | |
| CO$_2$-cyclopentyl | H | CH$_3$ | CH$_3$ | |
| CO$_2$-cyclohexyl | H | OCH$_3$ | OCH$_3$ | |
| CO$_2$CH$_2$CH$_2$OCH$_3$ | H | CH$_3$ | H | |
| CO$_2$(CH$_2$CH$_2$O)$_2$CH$_3$ | H | CH$_3$ | CH$_3$ | |
| CO$_2$(CH$_2$CH$_2$O)$_2$C$_2$H$_5$ | H | CH$_3$ | OCH$_3$ | |
| CO$_2$CH$_2$CH$_2$OC$_2$H$_5$ | H | OCH$_3$ | CH$_3$ | |
| CO$_2$(CH$_2$)$_3$OCH$_3$ | H | OCH$_3$ | OCH$_3$ | |
| CO$_2$(CH$_2$)$_3$OC$_2$H$_5$ | H | CH$_3$ | CH$_3$ | |
| SO$_2$CH$_3$ | H | CH$_3$ | CH$_3$ | |
| SO$_2$CH$_3$ | H | OCH$_3$ | CH$_3$ | |
| SO$_2$CH$_3$ | H | CH$_3$ | OCH$_3$ | |
| SO$_2$CH$_3$ | H | OCH$_3$ | CH(CH$_3$)$_2$ | |
| SO$_2$C$_2$H$_5$ | H | C$_2$H$_5$ | C$_2$H$_5$ | |
| SO$_2$CH(CH$_3$)$_2$ | H | CH$_3$ | OCH$_3$ | |
| SO$_2$(CH$_2$)$_2$CH$_3$ | H | OCH$_3$ | CH$_3$ | |
| SO$_2$(CH$_2$)$_3$CH$_3$ | H | OCH$_3$ | OCH$_3$ | |
| SO$_2$CH(CH$_3$)C$_2$H$_5$ | H | CH$_3$ | CH$_3$ | |
| SO$_2$OCH$_2$CF$_3$ | H | OCH$_3$ | CH$_3$ | |
| SO$_2$OCH$_2$CCl$_3$ | H | CH$_3$ | OCH$_3$ | |
| SO$_2$N(OCH$_3$)CH$_3$ | H | CH$_3$ | OC$_2$H$_5$ | |
| SO$_2$N(CH$_3$)$_2$ | H | CH$_3$ | CH$_3$ | |
| SO$_2$N(CH$_3$)$_2$ | H | CH$_3$ | OCH$_3$ | |
| SO$_2$N(CH$_3$)$_2$ | H | OCH$_3$ | CH$_3$ | |
| SO$_2$N(CH$_3$)C$_2$H$_5$ | H | OCH$_3$ | CH$_2$OCH$_3$ | |
| SO$_2$N(C$_2$H$_5$)$_2$ | H | OCH$_3$ | OCH$_3$ | |
| SO$_2$N(CH$_3$)(CH$_2$)$_3$CH$_3$ | H | CH$_3$ | CH$_3$ | |
| SO$_2$N[CH(CH$_3$)$_2$]CH$_3$ | H | CH$_3$ | OCH$_3$ | |
| SO$_2$N(CH$_3$)$_2$ | H | OCH$_3$ | (CH$_2$)$_3$CH$_3$ | |
| OCHF$_2$ | H | OCH$_3$ | OCH$_3$ | |
| OCF$_3$ | H | CH$_3$ | CH$_3$ | |
| OCH$_2$CF$_3$ | H | CH$_3$ | CF$_3$ | |
| OCF$_2$CHF$_2$ | H | CH$_3$ | Cl | |
| OCF$_2$CHFCl | H | CH$_3$ | OCH$_3$ | |
| OCF$_2$CHFBr | H | OCH$_3$ | CH$_3$ | |
| OCF$_2$CHFCF$_3$ | H | OC$_2$H$_5$ | OC$_2$H$_5$ | |
| SO$_2$CHF$_2$ | H | CH$_3$ | CH$_3$ | |
| SO$_2$CH$_2$CF$_3$ | H | CH$_3$ | OCH$_3$ | |
| SO$_2$CF$_3$ | H | OCH$_3$ | CH$_3$ | |
| SO$_2$CF$_2$CHF$_2$ | H | OCH$_3$ | OCH$_3$ | |
| SO$_2$CF$_2$CHFCF$_3$ | H | CH$_3$ | CH$_3$ | |
| OSO$_2$CH$_3$ | H | CH$_3$ | OCH$_3$ | |
| OSO$_2$CH$_3$ | H | CH$_3$ | CH$_3$ | |
| OSO$_2$C$_2$H$_5$ | H | CH$_3$ | OCH$_3$ | |
| OSO$_2$(CH$_2$)$_2$CH$_3$ | H | OCH$_3$ | CH$_3$ | |
| OSO$_2$(CH$_2$)$_3$CH$_3$ | H | OCH$_3$ | OCH$_3$ | |
| OSO$_2$CH$_2$Cl$_2$Cl | H | OCH$_3$ | CH$_3$ | |
| OSO$_2$CF$_3$ | H | CH$_3$ | CH$_3$ | |
| OSO$_2$CH$_2$CCl$_3$ | H | OCH$_3$ | H | |
| OSO$_2$CH$_2$CH$_2$CH$_2$Br | H | OCH$_3$ | CH$_3$ | |
| CH$_2$OCH$_3$ | H | CH$_3$ | CH$_3$ | |
| CH$_2$OC$_2$H$_5$ | H | CH$_3$ | OCH$_3$ | |
| CH$_2$O(CH$_2$)$_2$CH$_3$ | H | OCH$_3$ | CH$_3$ | |
| CH$_2$OC(CH$_3$)$_3$ | H | OCH$_3$ | OCH$_3$ | |
| CH$_2$OCH(CH$_3$)$_2$ | H | CH$_3$ | CH$_3$ | |
| CH$_2$OCH$_3$ | 3-OCH$_3$ | OCH$_3$ | CH$_3$ | |
| CH$_2$OCH$_3$ | H | CH$_3$ | OC$_2$H$_5$ | |
| CH$_2$OCH$_2$CH=CH$_2$ | H | CH$_3$ | OCH$_3$ | |
| CH$_2$OCH$_2$CH=CHCH$_3$ | H | CH$_3$ | CH$_3$ | |
| CH$_2$OCH$_2$C(CH$_3$)=CH$_2$ | H | OCH$_3$ | OCH$_3$ | |

TABLE IIa-continued $$\text{H}-\underset{R_1}{\underset{|}{\overset{R}{\overset{|}{\bigcirc}}}}-SO_2N=\overset{O-N}{\underset{N}{\overset{\diagup}{\diagdown}}}\overset{X}{\underset{N}{\overset{\diagdown}{\diagup}}}\overset{N}{\underset{Y}{\overset{\diagup}{\diagdown}}}$$

| R | $R_1$ | X | Y | m.p. (°C.) |
|---|---|---|---|---|
| $CH_2SO_2CH_3$ | H | $CH_3$ | $CH_3$ | |
| $CH_2SO_2CH_2CH_3$ | H | $OCH_3$ | $OCH(CH_3)_2$ | |
| $CH_2SO_2CH_3$ | H | $CH_3$ | $O(CH_2)_3CH_3$ | |
| $CH_2SO_2CH(CH_3)_2$ | H | $OCH_3$ | $OCH_3$ | |
| $CH_2SO_2(CH_2)_3CH_3$ | H | $CH_3$ | $OCH_3$ | |
| $CH_2SO_2CH_3$ | H | $OC_2H_5$ | $CH_3$ | |
| $CH_2SO_2(CH_2)_2CH_3$ | H | $C_2H_5$ | $OCH_3$ | |
| $CH_2OC_2H_5$ | 5-$OCH_3$ | $CH_3$ | $CH_3$ | |
| Cl | 5-$C_2H_5$ | $CH_3$ | $CH_3$ | |
| $CH_3$ | 5-$CH(CH_3)_2$ | $CH_3$ | $OCH_3$ | |
| $OCH_3$ | 5-$(CH_2)_3CH_3$ | $CH_3$ | $OCH_3$ | |
| Br | 3-$O(CH_2)_2CH_3$ | $OCH_3$ | $OCH_3$ | |
| F | 5-$CF_3$ | $OCH_3$ | $CH_3$ | |
| $CO_2CH_3$ | 5-$OC(CH_3)_3$ | $CH_3$ | $CH_3$ | |
| $CO_2CH_3$ | 5-$NO_2$ | $CH_3$ | $OCH_3$ | |

TABLE IIb $$\text{H}-\underset{R_1}{\underset{|}{\overset{R}{\overset{|}{\bigcirc}}}}-SO_2N=\overset{O-N}{\underset{N}{\overset{\diagup}{\diagdown}}}\overset{Y}{\underset{N}{\overset{\diagdown}{\diagup}}}\overset{N}{\underset{X}{\overset{\diagup}{\diagdown}}}$$

| R | $R_1$ | X | Y | m.p. (°C.) |
|---|---|---|---|---|
| Cl | H | $OCH_3$ | $CH_2OC_2H_5$ | |
| $CF_3$ | H | $CH_3$ | $CF_3$ | |
| $NO_2$ | H | $OCH_3$ | $CH_2CH_2OC_2H_5$ | |
| $NO_2$ | H | $OC_2H_5$ | $CH_2CH_2OCH_3$ | |
| $CO_2CH_3$ | H | $OCH_3$ | $O(CH_2)_3CH_3$ | |
| $CO_2CH_3$ | H | $CH_3$ | $OCH(CH_3)_2$ | |
| $CO_2CH_2CH_2OCH_3$ | H | $CH_3$ | H | |
| $SO_2CH_3$ | H | $OCH_3$ | $CH(CH_3)_2$ | |
| $SO_2N(CH_3)C_2H_5$ | H | $OCH_3$ | $CH_2OCH_3$ | |
| $SO_2N(CH_3)_2$ | H | $OCH_3$ | $(CH_2)_3CH_3$ | |
| $OCH_2CF_3$ | H | $CH_3$ | $CF_3$ | |
| $OSO_2CH_2CCl_3$ | H | $OCH_3$ | H | |
| $CH_2OCH_3$ | H | $OCH_3$ | $OC_2H_5$ | |
| $CH_2SO_2CH_3$ | H | $CH_3$ | $O(CH_2)_2CH_3$ | |
| $CO_2CH_3$ | H | $CH_3$ | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE III

| | Weight Percent* | | |
|---|---|---|---|
| | Active Ingredient | Inert Diluent(s) | Surfactant(s) |
| Wettable Powders | 20–90 | 0–74 | 1–10 |
| Oil Suspensions, | 3–50 | 40–95 | 0–15 |

TABLE III-continued

| | Weight Percent* | | |
|---|---|---|---|
| | Active Ingredient | Inert Diluent(s) | Surfactant(s) |
| Emulsions, Solutions, (including Emulsifiable Concentrates) | | | |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a surfactant or an inert diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid inert diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid inert diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions, i.e., formulations, are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No.

3,060,084). Granules and pellets can be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 11

Wettable Powder

| | |
|---|---|
| 2-Chloro-N—(5,7-dimethyl-2H—[1,2,4]oxadiazolo-[2,3-a]-pyrimidin-2-ylidene)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 12

Wettable Powder

| | |
|---|---|
| 2-Chloro-N—(5,7-dimethyl-2H—[1,2,4]oxadiazolo-[2,3-a]-pyrimidin-2-ylidene)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 13

Granule

| | |
|---|---|
| Wettable Powder of Example 10 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 14

Extruded Pellet

| | |
|---|---|
| 2-Chloro-N—(5,7-dimethyl-2H—[1,2,4]oxadiazolo-[2,3-a]-pyrimidin-2-ylidene)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 15

Oil Suspension

| | |
|---|---|
| 2-Chloro-N—(5,7-dimethyl-2H—[1,2,4]oxadiazolo-[2,3-a]-pyrimidin-2-ylidene)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 16

Wettable Powder

| | |
|---|---|
| 2-Chloro-N—(5,7-dimethyl-2H—[1,2,4]oxadiazolo-[2,3-a]-pyrimidin-2-ylidene)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles substantially all below about 100 microns, the material is reblended and sifted through a U.S.S. No. 50 sieve (0.3 mm opening) and packaged.

EXAMPLE 17

Low Strength Granule

| | |
|---|---|
| 2-Chloro-N—(5,7-dimethyl-2H—[1,2,4]oxadiazolo-[2,3-a]-pyrimidin-2-ylidene)benzenesulfonamide | 1% |
| chlorobenzene | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 18

Aqueous Suspension

| | |
|---|---|
| 2-Chloro-N—(5,7-dimethyl-2H—[1,2,4]oxadiazolo-[2,3-a]-pyrimidin-2-ylidene)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 19

Low Strength Granule

| | |
|---|---|
| 2-Chloro-N—(5,7-dimethyl-2H—[1,2,4]oxadiazolo-[2,3-a]-pyrimidin-2-ylidene)benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 20

Emulsifiable Concentrate

| | |
|---|---|
| 2-Chloro-N—(5,7-dimethyl-2H—[1,2,4]oxadiazolo-[2,3-a]-pyrimidin-2-ylidene)benzenesulfonamide | 30% |
| blend of oil soluble sulfonates and polyoxyethylene ethers | 4% |
| chlorobenzene | 66% |

The ingredients are combined and stirred with gentle warming to speed solution. A fine screen filter is included in packaging operation to insure the absence of any extraneous undissolved material in the product.

EXAMPLE 21

Granule

| | |
|---|---|
| 2-Chloro-N—(5,7-dimethyl-2H—[1,2,4]oxadiazolo-[2,3-a]-pyrimidin-2-ylidene)benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

EXAMPLE 22

High Strength Concentrate

| | |
|---|---|
| 2-Chloro-N—(5,7-dimethyl-2H—[1,2,4]oxadiazolo-[2,3-a]-pyrimidin-2-ylidene)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 23

Wettable Powder

| | |
|---|---|
| 2-Chloro-N—(5,7-dimethyl-2H—[1,2,4]oxadiazolo-[2,3-a]-pyrimidin-2-ylidene)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 24

Wettable Powder

| | |
|---|---|
| 2-Chloro-N—(5,7-dimethyl-2H—[1,2,4]oxadiazolo-[2,3-a]-pyrimidin-2-ylidene)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 25

Oil Suspension

| | |
|---|---|
| 2-Chloro-N—(5,7-dimethyl-2H—[1,2,4]oxadiazolo-[2,3-a]-pyrimidin-2-ylidene)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 26

Dust

| | |
|---|---|
| 2-Chloro-N—(5,7-dimethyl-2H—[1,2,4]oxadiazolo-[2,3-a]-pyrimidin-2-ylidene)benzenesulfonamide | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures.

The precise amount of the compounds of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. The higher rates of application from within this range will normally be selected for adverse conditions or where extended persistence in soil is desired.

The compounds of Formula I may be used in combination with any other commercial herbicide such as the triazine, triazole, uracil, urea, amide, diphenylether, carbamate and bipyridylium types.

The activity of these compounds was discovered in greenhouse tests. The tests are described and the data resulting from them are shown below.

Test A

Seeds of crabgrass (Digitaria spp.), barnywardgrass (*Echinochloa crusgalli*), wild oats (*Avena fatua*), sicklepod (*Cassia obtusifolia*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with the chemicals dissolved in a non-phytotoxic solvent solution of the compounds of Table A. At the same time, cotton having five leaves (including cotyledonary ones), bush beans with the third trifoliolate leaf expanding, crabgrass, barnyardgrass and wild oats with two leaves, sicklepod with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed with a non-phytotoxic solvent solution of the compounds of Table A. Other containers of the above untreated weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0 = no effect
10 = maximum effect
C = chlorosis or necrosis
D = defoliation
E = emergence inhibition
G = growth retardation
H = formative effects
6Y = abscised buds or flowers
U = unusual pigmentation and
X = axillary stimulation.

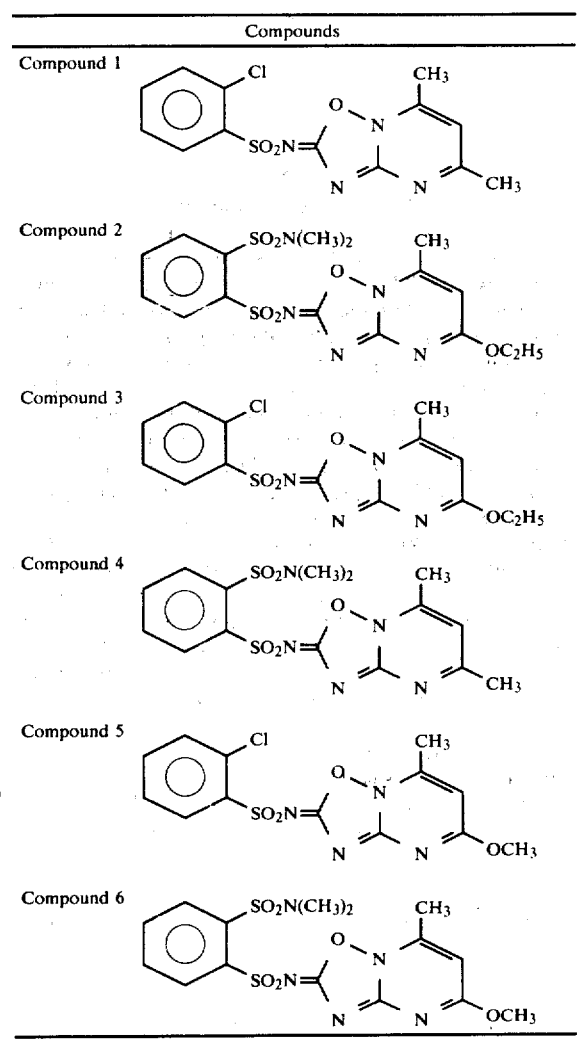

TABLE A

| Rate kg/ha | Cmpd. 1 0.4 | Cmpd. 2 0.4 | Cmpd. 2 0.05 | Cmpd. 3 0.4 | Cmpd. 4 0.4 | Cmpd. 5 0.4 | Cmpd. 6 0.4 | Cmpd. 6 0.05 |
|---|---|---|---|---|---|---|---|---|
| Post-emergence | | | | | | | | |
| Bushbean | 10D,9G,6Y | 9C | 9C | 9D,9G,6Y | 9C | 8D,9G,6Y | 9C, | 9C |
| Cotton | 3U,3C,9G | 5C,9G | 4C,9G | 3C,8G | 5C,9G | 5C,9G | 4C,8G | 5C,9G |
| Morningglory | 9C | 9C | 9C | 10C | 9C | 10C | 9C | 9C |
| Cocklebur | 9C | 9C | 1C,7H | 5G | 6C,9G | 9C | 9C | 9C |
| Cassia | 5C,9G | 9C | 6C,9G | 2C,7H | 9C | 9C | 6C,9G | 9C |
| Nutsedge | 6C,9G | 5C,9G | 5G | 1C,7G | 6C,9G | 6C,9G | 6C,9G | 8G,2C |
| Crabgrass | 1C,8G | 6C,9G | 4C,9G | 2C,5G | 6C,9G | 4C,8G | 9C | 4C,9G |
| Barnyardgrass | 6C,9G | 10C | 6C,9H | 5C,9H | 9C | 10C | 10C | 10C |
| Wild Oats | 3C,9G | 6C,9H | 2C,6G | 8G,5X | 4C,9G | 3C,9G | 5C,9G | 3C,9G |
| Wheat | 2C,9G | 3C,9G | 3C,9G | 8G,5X | 4C,9G | 2C,9G | 5C,9G | 3C,9G |
| Corn | 6U,9G | 3U,9G | 4C,9H | 6U,9G | 10C | 10C | 5C,9G | 4C,9G |
| Soybean | 5C,9G | 9C | 6C,9G | 10C | 9C | 9C | 9C | 9C |
| Rice | 6C,9G | 5C,9G | 5C,9G | 6C,9G | 6C,9G | 6C,9G | 6C,9G | 6C,9G |
| Sorghum | 10C | 4C,9G | 3C,9G | 2C,9G | 9C | 5C,9G | 9C | 9C |
| Pre-emergence | | | | | | | | |
| Morningglory | 9G | 9C | 3C,9G | 3C,9G | 9H | 9C | 9C | 4C,9G |

TABLE A-continued

| Rate kg/ha | Cmpd. 1 0.4 | Cmpd. 2 0.4 | Cmpd. 2 0.05 | Cmpd. 3 0.4 | Cmpd. 4 0.4 | Cmpd. 5 0.4 | Cmpd. 6 0.4 | Cmpd. 6 0.05 |
|---|---|---|---|---|---|---|---|---|
| Cocklebur | 3C,9H | 9H,6C | 9H,3C | 2C | 9H | 9H | 9H | 9H |
| Cassia | 3C,9G | 9C | 6C,9G | 3C,7G | 8H,5C | 3C,9G | 9C | 5C,9G |
| Nutsedge | 3C,9G | 5C,8G | 2C,7G | 2C | 3C,9G | 2C,5G | 5C,9G | 3C,7G |
| Crabgrass | 3C,8G | 6C,9G | 3C,8H | 2C,8G | 3C,8G | 5C,8G | 6C,9G | 4C,7G |
| Barnyardgrass | 3C,9H | 6C,9H | 4C,9H | 5C,9H | 9H | 5C,9H | 6C,9H | 5C,9H |
| Wild Oats | 2C,8G | 6C,9G | 5C,9G | 2C,8G | 3C,9H | 4C,8G | 5C,9G | 3C,9G |
| Wheat | 8G | 6C,9G | 3C,8G | 1C,7G | 2C,9H | 3C,9G | 3C,9G | 3C,9G |
| Corn | 9G | 6C,9H | 3C,9H | 3C,9H | 2C,9H | 3C,9G | 2C,9G | 3C,9G |
| Soybean | 2C,6H | 5C,8H | 4C,8H | 2C,6H | 2C,8H | 4C,7H | 5C,8H | 4C,7H |
| Rice | 10E | 5C,9H | 5C,9H | 9H | 10E | 10E | 10E | 5C,9H |
| Sorghum | 6C,9H | 6C,9H | 5C,9G | 5C,9H | 2C,9H | 5C,9H | 5C,9H | 5C,9H |

Test B

Two plastic bulb pans were filled with fertilized and limed Fallsington slit loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B.

TABLE B
PRE-EMERGENCE ON FALLSINGTON SILT LOAM SOIL

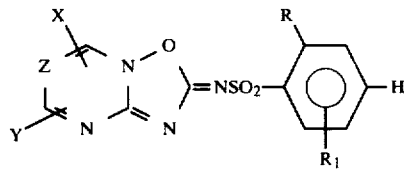

| Pre-Emergence | 0.25 kg/ha | 0.06 kg/ha |
|---|---|---|
| Rice | 6G,7E | 6G |
| Barnyardgrass | 4G,2C | 0 |
| Wheat | 3G | 0 |
| Wild Oats | 0 | 0 |
| Crabgrass | 0 | 0 |
| Sorghum | 8G,5H | 4G,3H |
| Johnsongrass | 5G,3H | 2G |
| Dallasgrass | 4G | 3G |
| Giant Foxtail | 3G | 3G |
| Bluegrass | 3G | 0 |
| Cheatgrass | 4G | 0 |
| Corn | 3G | 0 |
| Mustard | 8G,8C | 0 |
| Cocklebur | — | 0 |
| Pigweed | 7G | 0 |
| Nutsedge | 3G | 0 |
| Cotton | 2G | 0 |
| Morningglory | 0 | 0 |
| Cassia | 2G | 0 |

TABLE B-continued
PRE-EMERGENCE ON FALLSINGTON SILT LOAM SOIL

| Pre-Emergence | 0.25 kg/ha | 0.06 kg/ha |
|---|---|---|
| Teaweed | 0 | 0 |
| Velvetleaf | 0 | 0 |
| Jimsonweed | 0 | 0 |
| Soybean | 0 | 0 |
| Sugarbeet | 4G | 2G |

What is claimed is:

1. A compound of the formula:

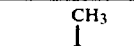

where

R is $C_1$–$C_4$ alkyl, $C_1$–$C_4$ alkoxy, F, Cl, Br, $NO_2$, $COR_4$, $SO_2R_5$, $SO_2NR_6R_7$, $SO_2OCH_2CF_3$, $SO_2OCH_2CCl_3$, $SO_2N(OCH_3)(CH_3)$, $BR_8$, $OSO_2R_9$ or $CH_2P$;

$R_1$ is H, F, Cl, Br, $CF_3$, $NO_2$, $C_1$–$C_4$ alkyl or $C_1$–$C_4$ alkoxy;

$R_4$ is $C_1$–$C_6$ alkoxy, $C_3$–$C_6$ alkenyloxy, $C_2$–$C_6$ haloalkoxy substituted with 1–3 atoms selected from F, Cl, or Br, $C_5$–$C_6$ cycloalkoxy, —$O(CH_2CH_2O)_nR_{10}$ or $OCH_2CH_2CH_2OR_{10}$;

n is 1 or 2;

$R_5$ is $C_1$–$C_4$ alkyl;

$R_6$ and $R_7$ are independently $C_1$–$C_4$ alkyl, provided the total number of carbon atoms of $R_6$ and $R_7$ does not exceed 5;

B is O or $SO_2$;

$R_8$ is $CHF_2$, $CF_3$, $CH_2CF_3$, $CF_2CHFG$ where G is F, Cl, Br or $CF_3$;

$R_9$ is $C_1$–$C_4$ alkyl or $C_1$–$C_4$ alkyl substituted with 1–3 atoms selected from F, Cl or Br;

P is $C_1$–$C_4$ alkoxy, $C_3$–$C_4$ alkenyloxy or $SO_2R_5$;

$R_{10}$ is $CH_3$ or $CH_3CH_2$;

X is $CH_3$, $CH_3CH_2$, $CH_3O$ or $CH_3CH_2O$;

Y is H, Cl, $CF_3$, $C_1$–$C_4$ alkyl, $C_1$–$C_4$ alkoxy, $CH_2OCH_3$, $CH_2OCH_2CH_3$, $CH_2CH_2OCH_3$ or $CH_2CH_2OCH_2CH_3$; and Z is CH and their agriculturally suitable salts.

2. A compound of claim 1 wherein R is $C_1$-$C_4$ alkyl, $C_1$-$C_4$ alkoxy, F, Cl, Br, $CF_3$, $SO_2R_5$, $BR_8$, $OSO_2R_9$ or $CH_2P$, where P is $C_1$-$C_4$ alkoxy and $R_1$ is H, F, Cl, Br, $CF_3$, $C_1$-$C_4$ alkyl or $C_1$-$C_4$ alkoxy.

3. A compound of claim 2 wherein $R_1$ is H.

4. A compound of claim 3 wherein R is $C_1$-$C_3$ alkyl, $C_1$-$C_3$ alkoxy, F, Cl, Br, $CF_3$, $SO_2R_5$, $BR_8$, $OSO_2R_9$ or $CH_2P$; provided that:

(a) when R is $SO_2R_5$, then $R_5$ is $C_1$-$C_3$ alkyl;
(b) when R is $BR_8$, then $BR_8$ is $SO_2CF_3$ or $OCF_2CF_2H$;
(c) when R is $OSO_2R_9$, then $R_9$ is $C_1$-$C_3$ alkyl or $CF_3$; and
(d) when R is $CH_2P$, then P is $CH_3O$.

5. A compound of claim 4 wherein Y is H, $CF_3$, $C_1$-$C_2$ alkyl, $C_1$-$C_2$ alkoxy or $CH_2OCH_3$.

6. A compound of claim 5 wherein X is $CH_3$ or $CH_3O$ and Y is $CH_3$ or $CH_3O$.

7. The compound of claim 1, 2-Chloro-N-(5,7-dimethyl-2H-[1,2,4]oxadiazolo[2,3-a]pyrimidin-2-yl-idene)benzenesulfonamide.

8. The compound of claim 1, 2-Chloro-N-(5-methoxy-7-methyl-2H-[1,2,4]oxadiazolo[2,3-a]pyrimidin-2-ylidene)benzenesulfonamide.

9. The compound of claim 1, N',N'-dimethyl-N-(5,7-dimethyl-2H-1,2,4-oxadiazolo[2,3-A]pyrimidin-2-yl)-1,2-benzenedisulfonamide.

10. The compound of claim 1, N',N'-dimethyl-N-(5-methoxy-7-methyl-2H-1,2,4-oxadiazolo[2,3-A]pyrimidin-2-yl)-1,2-benzenedisulfonamide.

11. A compound of the formula:

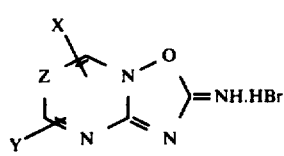

wherein
X is $CH_3$, $CH_3CH_2$, $CH_3O$ or $CH_3CH_2O$;
Y is H, Cl, $CF_3$, $C_1$-$C_4$ alkyl, $C_1$-$C_4$ alkoxy, $CH_2OCH_3$, $CH_2OCH_2CH_3$, $CH_2CH_2OCH_3$ or $CH_2CH_2OCH_2CH_3$; and Z is CH.

12. The compound of claim 11 wherein Y is H, $CF_3$, $C_1$-$C_2$ alkyl, $C_1$-$C_2$ alkoxy or $CH_2OCH_3$.

13. The compound of claim 12 wherein X is $CH_3$ or $CH_3O$, and Y is $CH_3$ or $CH_3O$.

14. A composition suitable for controlling the growth of undesired vegetation consisting essentially of an effective amount of a compound of claim 1 and at least one of a surfactant and a solid or liquid inert diluent.

15. A composition suitable for controlling the growth of undesired vegetation consisting essentially of an effective amount of a compound of claim 2 and at least one of a surfactant and a solid or liquid inert diluent.

16. A composition suitable for controlling the growth of undesired vegetation consisting essentially of an effective amount of a compound of claim 3 and at least one of a surfactant and a solid or liquid inert diluent.

17. A composition suitable for controlling the growth of undesired vegetation consisting essentially of an effective amount of a compound of claim 4 and at least one of a surfactant and a solid or liquid inert diluent.

18. A composition suitable for controlling the growth of undesired vegetation consisting essentially of an effective amount of a compound of claim 5 and at least one of a surfactant and a solid or liquid inert diluent.

19. A composition suitable for controlling the growth of undesired vegetation consisting essentially of an effective amount of a compound of claim 6 and at least one of a surfactant and a solid or liquid inert diluent.

20. A composition suitable for controlling the growth of undesired vegetation consisting essentially of an effective amount of the compound of claim 7 and at least one of a surfactant and a solid or liquid inert diluent.

21. A composition suitable for controlling the growth of undesired vegetation consisting essentially of an effective amount of the compound of claim 8 and at least one of a surfactant and a solid or liquid inert diluent.

22. A composition suitable for controlling the growth of undesired vegetation consisting essentially of an effective amount of the compound of claim 9 and at least one of a surfactant and a solid or liquid inert diluent.

23. A composition suitable for controlling the growth of undesired vegetation consisting essentially of an effective amount of the compound of claim 10 and at least one of a surfactant and a solid or liquid inert diluent.

24. A method for controlling the growth of undesired vegetation which comprises applying to the locus to be protected an effective amount of a compound of claim 1.

25. A method for controlling the growth of undesired vegetation which comprises applying to the locus to be protected an effective amount of a compound of claim 2.

26. A method for controlling the growth of undesired vegetation which comprises applying to the locus to be protected an effective amount of a compound of claim 3.

27. A method for controlling the growth of undesired vegetation which comprises applying to the locus to be protected an effective amount of a compound of claim 4.

28. A method for controlling the growth of undesired vegetation which comprises applying to the locus to be protected an effective amount of a compound of claim 5.

29. A method for controlling the growth of undesired vegetation which comprises applying to the locus to be protected an effective amount of a compound of claim 6.

30. A method for controlling the growth of undesired vegetation which comprises applying to the locus to be protected an effective amount of the compound of claim 7.

31. A method for controlling the growth of undesired vegetation which comprises applying to the locus to be protected an effective amount of the compound of claim 8.

32. A method for controlling the growth of undesired vegetation which comprises applying to the locus to be protected an effective amount of the compound of claim 9.

33. A method for controlling the growth of undesired vegetation which comprises applying to the locus to be protected an effective amount of the compound of claim 10.

* * * * *